US010791950B2

(12) United States Patent
Mest

(10) Patent No.: US 10,791,950 B2
(45) Date of Patent: Oct. 6, 2020

(54) IN-VIVO CALIBRATION OF CONTACT FORCE-SENSING CATHETERS USING AUTO ZERO ZONES

(75) Inventor: Robert Alan Mest, Long Beach, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 983 days.

(21) Appl. No.: 13/249,384

(22) Filed: Sep. 30, 2011

(65) Prior Publication Data

US 2013/0085416 A1    Apr. 4, 2013

(51) Int. Cl.
| | | |
|---|---|---|
| A61B 5/042 | (2006.01) | |
| A61B 5/06 | (2006.01) | |
| A61B 5/00 | (2006.01) | |
| G01L 25/00 | (2006.01) | |
| A61B 18/00 | (2006.01) | |
| A61B 18/14 | (2006.01) | |
| A61B 17/00 | (2006.01) | |
| A61B 90/00 | (2016.01) | |

(52) U.S. Cl.
CPC .............. *A61B 5/042* (2013.01); *A61B 5/062* (2013.01); *A61B 5/6885* (2013.01); *G01L 25/00* (2013.01); *A61B 18/1492* (2013.01); *A61B 2017/00725* (2013.01); *A61B 2018/00357* (2013.01); *A61B 2018/00577* (2013.01); *A61B 2018/00839* (2013.01); *A61B 2090/065* (2016.02); *A61B 2560/0223* (2013.01)

(58) Field of Classification Search
CPC ....... A61B 5/042; A61B 5/6885; A61B 5/062; A61B 18/1492; A61B 2018/00357; A61B 2018/00577; A61B 2018/00839; A61B 2017/00725; A61B 2019/465; G01L 25/00
USPC ....... 600/433–435, 585; 604/164.13; 606/34, 606/41, 48; 607/96–102
See application file for complete search history.

(56) References Cited

U.S. PATENT DOCUMENTS

| 5,391,199 A | 2/1995 | Ben-Haim |
| 5,840,025 A | 11/1998 | Ben-Haim |

(Continued)

FOREIGN PATENT DOCUMENTS

| CN | 102085117 A | 6/2011 |
| CN | 101947130 B | 2/2015 |

(Continued)

OTHER PUBLICATIONS

U.S. Appl. No. 12/938,458, filed Nov. 3, 2010 Ludwin et al.
(Continued)

*Primary Examiner* — Rene T Towa

(57) ABSTRACT

A method for the in vivo re-calibration of a force sensing probe such as an electrophysiology catheter provides for the generation of an auto zero zone. The distal tip of the catheter or other probe is placed in a body cavity within the patient. Verification that there is no tissue contact is made using electrocardiogram (ECG) or impedance data, fluoroscopy or other real-time imaging data and/or an electro-anatomical mapping system. Once verification that there is no tissue contact is made, the system recalibrates the signal emanating from the force sensor setting it to correspond to a force reading of zero grams and this recalibrated baseline reading is used to generate and display force readings based on force sensor data.

26 Claims, 3 Drawing Sheets

(56) References Cited

U.S. PATENT DOCUMENTS

| | | |
|---|---|---|
| 6,239,724 B1 | 5/2001 | Doron et al. |
| 6,266,551 B1 * | 7/2001 | Osadchy et al. ............... 600/424 |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2002/0165448 A1 | 11/2002 | Ben-Haim |
| 2003/0120150 A1 | 6/2003 | Govari |
| 2003/0158477 A1 * | 8/2003 | Panescu ........................ 600/424 |
| 2004/0068178 A1 | 4/2004 | Govari |
| 2006/0025837 A1 * | 2/2006 | Stern et al. ..................... 607/99 |
| 2007/0100332 A1 | 5/2007 | Paul et al. |
| 2008/0177175 A1 * | 7/2008 | Mottola et al. ............... 600/424 |
| 2009/0076476 A1 | 3/2009 | Barbagli et al. |
| 2009/0093806 A1 | 4/2009 | Govari et al. |
| 2009/0138007 A1 | 5/2009 | Govari et al. |
| 2009/0247993 A1 * | 10/2009 | Kirschenman et al. ........... 606/1 |
| 2010/0063478 A1 * | 3/2010 | Selkee ........................... 604/524 |
| 2010/0121138 A1 | 5/2010 | Goldenberg et al. |
| 2010/0298826 A1 * | 11/2010 | Leo et al. ........................ 606/41 |
| 2011/0137153 A1 | 6/2011 | Govari et al. |
| 2012/0158011 A1 * | 6/2012 | Sandhu et al. ................ 606/130 |
| 2014/0194869 A1 | 7/2014 | Leo et al. |

FOREIGN PATENT DOCUMENTS

| | | | |
|---|---|---|---|
| EP | 0 904 796 A2 | | 3/1999 |
| EP | 2332461 A1 | | 6/2011 |
| JP | 08-043220 | * | 2/1996 |
| WO | WO 96/05768 | | 2/1996 |
| WO | WO 06/135483 A2 | | 12/2006 |
| WO | WO 07/015139 A2 | | 2/2007 |
| WO | WO 07/098494 A1 | | 8/2007 |
| WO | WO 2010/1444419 A2 | | 12/2010 |

OTHER PUBLICATIONS

Partial European Search Report dated Sep. 30, 2013 for corresponding Application No. EP12186529.

European Search Report dated Oct. 10, 2014 from corresponding European Patent Application No. 14180525.9.

Search Report issued by the Peoples Republic of China for Application No. 201210378085.8 dated Aug. 3, 2015.

Japanese Notification of Reasons for Refusal dated Aug. 9, 2016 from corresponding Japanese Patent Application No. 2012-216130.

European Search Report for corresponding EPA No. 13199310.7 dated Jun. 8, 2017.

* cited by examiner

IN-VIVO CALIBRATION OF CONTACT FORCE-SENSING CATHETERS USING AUTO ZERO ZONES

FIELD OF INVENTION

The present invention relates to a method of using medical probes, such as catheters, particularly force-sensing catheters, for the treatment of the human body, particularly the treatment of cardiac arrhythmias. More particularly, the present invention relates to the dynamic, in-vivo, calibration of force-sensing probes or catheters in use during cardiac procedures.

BACKGROUND OF INVENTION

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/006455 and 2003/0120150 and 2004/0068178, whose disclosures are all incorporated herein by reference.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

One type of arrhythmia, atrial fibrillation, occurs when the normal electrical impulses generated by the sinoatrial node are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. Risk increases with age. Approximately 8% of people over 80 having some amount of AF. Atrial fibrillation is often asymptomatic and is not in itself generally life-threatening, but it may result in palpatations, weakness, fainting, chest pain and congestive heart failure. Stroke risk increases during AF because blood may pool and form clots in the poorly contracting atria and the left atrial appendage. The first line of treatment for AF is medication that either slow the heart rate or revert the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation. Such ablation is not successful in all patients, however. Thus, there is a need to have an alternative treatment for such patients. Surgical ablation is one option but also has additional risks traditionally associated with surgery.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a tip electrode at its distal end into a heart chamber. A reference electrode is provided, generally taped to the skin of the patient or by means of a second catheter that is positioned in or near the heart. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, 2009/0093806 and 2009/0138007, whose disclosures are incorporated herein by reference describe methods of sensing contact pressure between the distal tip of a catheter and tissue in a body cavity using a force sensor embedded in the catheter.

Co-pending and commonly assigned U.S. patent application Ser. No. 12/938,458 by Turgeman et al. entitled "Zero-Drift Detection and Correction in Contact Force Measurements" discloses and claims a method for setting a baseline reading for the force sensor in such catheters for use in future measurements based on detecting a plurality of measurements indicative of the force applied to the force sensor and determining that the measurements have not varied by more than a pre-defined amount.

SUMMARY OF THE INVENTION

The present invention is directed to a system and method for the calibration of force sensing catheters or other probes while in use in a patient.

The present method for calibrating a probe having a force sensor near the distal end of the probe starts with inserting the probe into a body cavity of a patient. A first signal from the force sensor indicative of the force being applied to the distal end of the probe is received by a processor operably connected to the probe. A verification that the distal tip of the probe is not in contact with tissue of the patient must be made and then the processor sets the first signal emanating from the probe equivalent to a force reading of zero. Subsequent readings of the signals from the force sensor are then adjusted based on this re-calibrated baseline for zero grams of force, i.e., no tissue contact.

In further steps of the method location information from the probe is received at the signal processor that is indicative of the location of the distal tip of the probe in three-dimensional space. This location of the distal tip of the probe is set as a location of a zero zone after verification that the probe is not in contact with the tissue of the body cavity of the patient. Verification can be done automatically or with user input. For example, the zero zone can be automatically created by recording locations that show zero grams of force and that are greater than a threshold distance (d) away from the reconstructed geometry in an electro-anatomic mapping system. In this way the reconstructed geometry plus location data can be used while the reading is still zero soon after resetting to expand the auto zero zone from a single point into a larger three dimensional space.

This stored zeroing zone location information can then be used in two ways. First the probe may be manipulated to a stored zeroing zone location where the processor receives an additional signal from the force sensor indicative of the force being applied to the distal end of the probe at that moment. Because the probe is assumed to be out of contact with the tissue of the patient at this stored zeroing zone location the processor sets the reading of this signal from the force sensor to be equivalent to a force reading of zero.

Alternatively, the location of the distal tip of the probe may be continuously monitored and when the location is equivalent to a stored zeroing zone location the signal received from the force sensor indicative of the force being applied to the distal end of the probe is automatically recalibrated to a force reading of zero.

The step of verifying whether or not the probe is in contact with the tissue of the patient can be accomplished using at least one of electrocardiogram data, electrode impedance data, fluoroscopic imaging, real-time MRI, real-time CT or electro-anatomic mapping to determine of the distal tip of the probe is in contact with tissue. The step of receiving location information regarding the distal tip of the catheter can include receiving the three-dimensional (x, y, z) spatial coordinates and pitch, roll and yaw of a location sensor such as a magnetic location sensor.

The novel method can be applied to cardiac catheters, including, but not limited to electrophysiology ablation catheters used in the chambers of a heart. Where the cardiac catheter is an ablation catheter having an electrode at or near the tip, such electrode(s) can also be used to record ECG data and/or impedance data. Unlike other force-sensing calibration procedures, this method can be used during a cardiac procedure.

Similarly, a system for re-calibrating force sensing probes includes a probe capable of being inserted into the body cavity of a patient and comprising a force sensor that provides a plurality of signals indicative of the force applied to the probe as the force varies over time. The system further includes a means for determining if the probe is in contact with tissue in the body cavity of the patient. A signal processor is configured to receive the plurality of signals indicative of the force and generate a force reading indicative of the force on the probe. The signal processor sets the force reading to zero when the means for determining if the probe is in contact determines that there is no contact between the probe and the body cavity of the patient.

The system further includes a location sensor capable of providing the processor with a plurality of electrical signals indicative of the location of the probe within three dimensional space and wherein the location of the probe is stored in memory as a zeroing zone when there is no contact between the probe and the body cavity of the patient at the given location. The processor automatically monitors the location of the probe and resets the force reading to zero (or warns the user to check and reset to the baseline reading to zero) when the probe is at a location stored in memory as a zero zone. The system user determines contact between the catheter and the tissue of the patient based on various inputs such as the electrocardiogram or impedance signals from at least one of the electrodes on the probe or fluoroscopic, real-time CT or real-time MRI images or information and images from an electro-anatomic mapping system. The system stores zeroing zone locations with information regarding the point in the cardiac cycle at which the location information was taken. Additionally, the system stores zeroing zone locations with information regarding the point in respiratory cycle at which the location information was taken.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Many diagnostic and therapeutic procedures, such as cardiac ablation and intracardiac electroanatomic mapping, use a minimally invasive probe, such as a catheter, which has at least one electrode mounted on its distal tip. The electrode is typically operated when the probe is pressed against a body cavity surface, such as the endocardium in the treatment of cardiac arrhythmias. It is important to the user of the catheter or probe, such as the electro-physiologist, to know that there is contact between the catheter and the tissue and to know the amount of force the catheter is asserting on the tissue. Newer force-sensing catheters provide such force measurement feedback to the user.

To accurately measure a force exerted by the distal tip on the endocardium, the force sensor is typically calibrated during manufacture to produce a reading of zero grams of force when there is no contact between the catheter and another object such as the tissue. Once this calibration is done, and baseline information from the force-sensing catheter has been determined, later measurements from the force sensor can be used to provide a value of the force exerted on the tip of the catheter.

Because force sensors in force-sensing catheters use analog components, the sensors are subject to changes in environmental conditions such as temperature and humidity, as well as to changes due to the aging of the components. Such changes may cause the force-sensing catheters to no longer be calibrated to the proper baseline for zero grams of force thereby introducing inaccuracies into the sensed force shown to the user of the catheter. In order to ensure accurate force values, the system and method of the present invention provide for an automatic re-calibration of the force-sensing catheter in pre-determined auto zero zones. A zeroing zone is detected by determining a plurality of catheter tip positions where the tip is not in contact with tissue. This can be done by using electrocardiogram (ECG) or impedance signals, fluoroscopic, real-time CT or real-time MRI imaging systems and/or an electroanatomic map or a combination of these modalities to determine whether or not there is contact between the tissue and the tip of the catheter. If the system, and alternatively the user, confirms that there is no tissue contact this location is determined to be an auto zero zone location where the force-sensing catheter can be recalibrated so that the baseline reading is zero grams of force, thereby compensating for any calibration drift.

Figure 1:
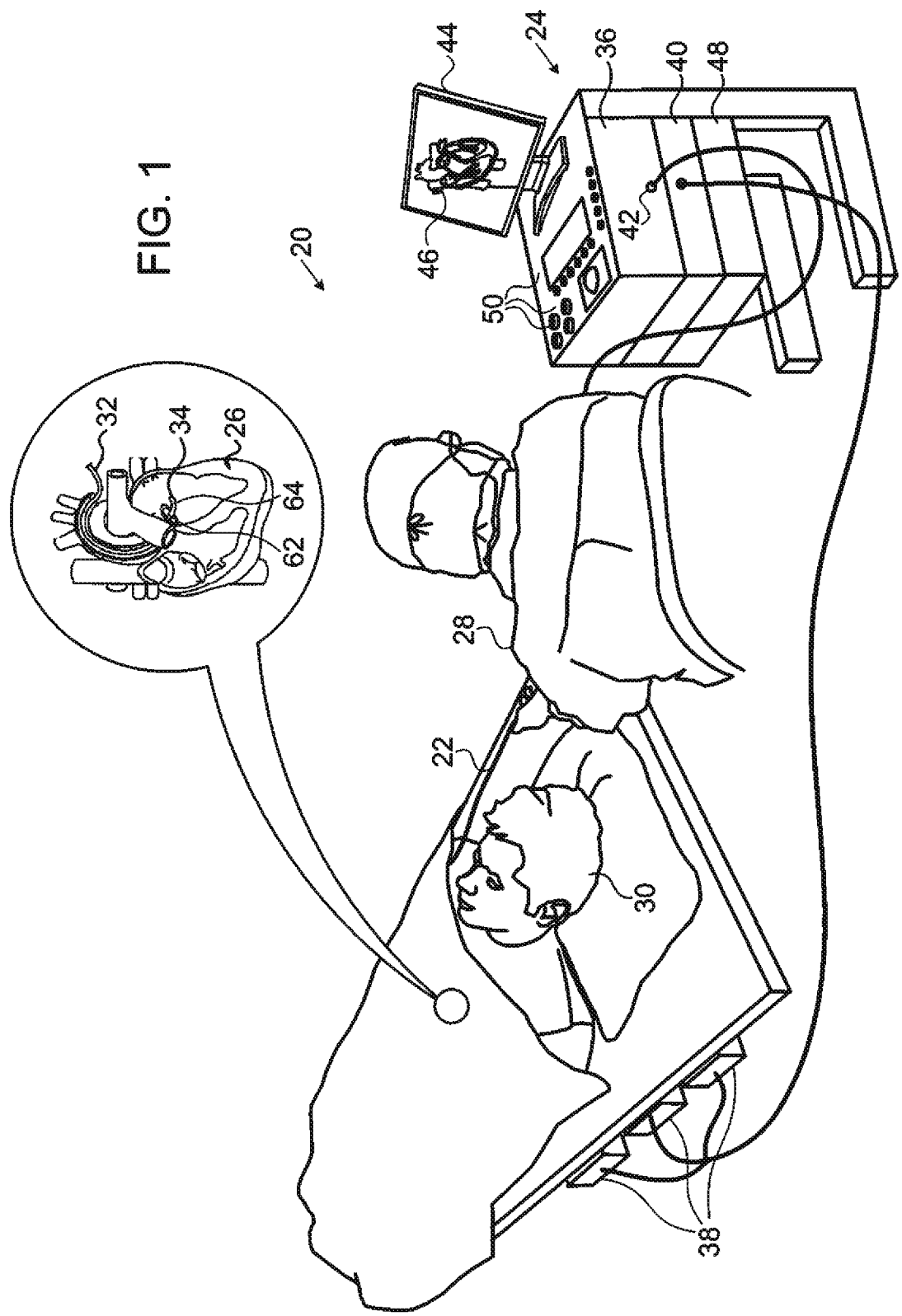
FIG. 1 is a schematic, pictorial illustration of an automatic calibration system for use with a force-sensing catheter in accordance with an embodiment of the present invention.

FIG. 1 is an illustration of a medical system 20 that uses auto zero zone calibration compensation in accordance with an embodiment of the present invention. System 20, particularly control console 24, may be based, for example, on the Carto™ systems produced by Biosense Webster, Inc. of Diamond Bar, Calif. System 20 comprises a probe 22, such as an EP ablation or mapping catheter, and a control console 24. In the embodiment described herein, it is assumed that probe 22 is used for diagnostic or therapeutic treatment, such as for mapping electrical potentials in a heart 26 or for performing ablation of endocardial or other tissue of heart 26. However, such a probe 22 may have other uses in the heart or other organs or vasculature of a patient.

An operator 28, such as a cardiologist, electrophysiologist or interventional radiologist inserts probe 22 through the vascular system of a patient 30 so that a distal end 32 of probe 22 enters a chamber of heart 26 (or other body cavity or vasculature). Operator 28 advances probe 22 so that the distal tip 34 of probe 22 engages endocardial tissue at a desired location or locations. Probe 22 is typically connected by a suitable connector at its proximal end to console 24.

Console 24 typically uses magnetic location sensing to determine location coordinates of distal end 32 inside heart 26. For this purpose, a driver circuit 36 in console 24 drives magnetic field generators 38 to generate magnetic fields within the body of patient 30. Typically, the field generators 38 comprise coils, which are placed below the patient's torso at known locations external to the patient 30. These coils generate magnetic fields in a predefined working volume that contains heart 26. A magnetic field sensor 62 within distal end 32 of probe 22 (shown in FIG. 2) generates electrical signals in response to these magnetic fields. A signal processor 40 processes these signals in order to determine the location coordinates of the distal end, typically including both location (x, y, z) and orientation (roll, pitch, yaw) coordinates. This method of location sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Signal processor 40 typically comprises a general-purpose computer, with suitable front end and interface circuits for receiving signals from probe 22 and controlling the other components of console 24. The processor 40 may be programmed in software to carry out the functions that are described herein. The software may be downloaded to console 24 in electronic form, over a network, for example, or it may be provided on tangible media, such as optical, magnetic or electronic memory media. Alternatively, some or all of the functions of processor 40 may be carried out by dedicated or programmable digital hardware components. Based on the signals received from the probe 22 and other components of system 20, processor 40 drives a display 44 to give operator 28 visual feedback through image 46 regarding the location of distal end 32 in the patient's body, as well as status information and guidance regarding the procedure that is in progress.

Alternatively or additionally, system 20 may comprise an automated mechanism for maneuvering and operating probe 22 within the body of patient 30. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 40 generates a control input for controlling the motion of the catheter based on the signals provided by the magnetic field sensor in the catheter. These signals are indicative of both the location of the distal end of the catheter and of force exerted on the distal end, as explained further hereinbelow.

Processor 40 stores data representing image 46 in a memory 48. In some embodiments, operator 28 can manipulate image 46 using one or more input devices 50. Although FIG. 1 shows a particular system configuration, other system configurations can also be employed to implement embodiments of the present invention, and are this considered to be within the spirit and the scope of this invention. For example, the methods described hereinbelow may be applied using location transducers of the types other than the magnetic field sensor described above, such as impedance based or ultrasonic location sensors. The term "location transducer" as used herein refers to an element mounted on probe 22 which causes console 24 to receive signals indicative of the coordinates of the element. The locations transducer may comprise a receiver on the probe that generates a location signal to the control unit based on the energy received by the transducer or it may comprise a transmitter, emitting energy that is sensed by a receiver external to the probe. Furthermore, the methods described hereinbelow may similarly be applied to therapeutic and diagnostic applications using not only catheters, but also other types of probes in the heart as well as in other organs and vasculature in the human body.

Figure 2:
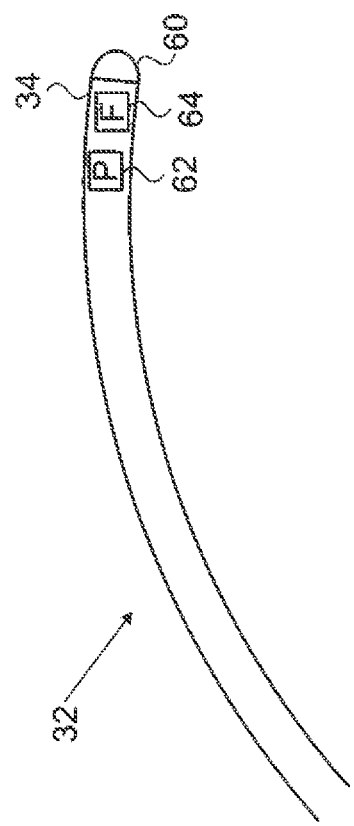
FIG. 2 is a schematic side view showing details of the distal portion of the force-sensing catheter, in accordance with an embodiment of the present invention.

In the present embodiment, processor 40 monitors the signal measurements received from a force sensor 64 within distal end 32 of probe 22. FIG. 2 is a schematic sectional view of the distal end 32 of probe 22 in accordance with an embodiment of the present invention. Specifically, FIG. 2 shows the functional elements of the distal end 32 of probe 22 used for therapeutic and/or diagnostic activity. An electrode 60 (e.g. an ablation electrode) at the distal tip 34 of the probe 22 is typically made of a metallic material such as a platinum/iridium alloy or another suitable biocompatible metal such as gold or gold alloy. Alternatively, multiple electrodes (not shown) along the length of the probe may be used for this purpose, such as a plurality of ring electrodes.

Location sensor (P) 62 transmits a signal to console 24 that is indicative of the location coordinates of the distal end 32 of probe 22. Location sensor 62 may comprise one or more miniature coils, and typically comprises multiple coils oriented along different axes. Alternatively, location sensor 62 may comprise wither another type of magnetic sensor, an electrode that serves as a location transducer, or location transducers of other types, such as impedance-based or ultrasonic location sensors. Although FIG. 2 shows a probe with a single location sensor 62, embodiments of the present invention may also utilize proves with more than one location sensor.

In an alternative embodiment, the roles of the location sensor 62 and magnetic field generators 38 may be reversed. Driver circuit 36 may drive magnetic field generators in the distal end 32 of probe 22 to generate one or more magnetic fields. The coils in generator 38 may be configured to sense the fields and generate signals indicative of the amplitude of the components of these magnetic fields. Processor 40 then receives and processes these signals in order to determine the location coordinates of the distal end 32 of probe 22 within heart 26.

Force sensor 64 measures a force applied by distal tip 34 to the endocardial (or other) tissue of the heart 26 by conveying a signal to the console that is indicative of the force exerted by the distal tip 34 on the intra-body tissue. In one embodiment, the force sensor 64 comprises a magnetic field transmitter and a receiver separated by a spring or helically cut tube in distal end 32. The information received by the processor 40 from the receiver is used to generate an indication of the force based on measuring the deflection of the spring. Such a force sensor 64 may be constructed in accordance with U.S. Patent Publication Nos. 2009/0093806 and 2009/0138007 whose disclosures are incorporated by reference herein. Alternatively, distal end 32 may comprise some other type of force sensor 64 capable of providing such an indication of the force.

Figure 3:
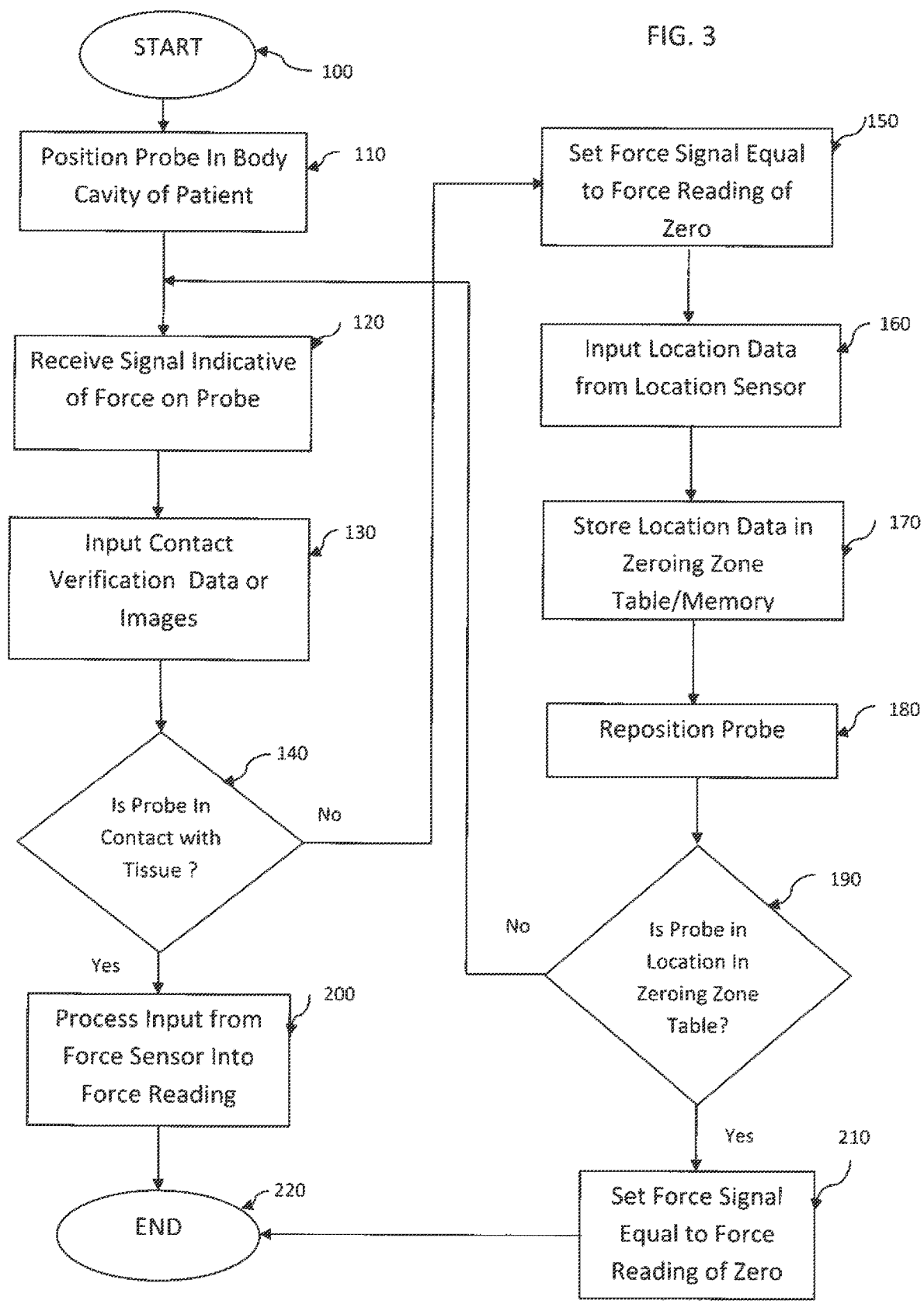
FIG. 3 is a flow diagram that illustrates a method of calibration of a force-sensing catheter in accordance with an embodiment of the present invention.

FIG. 3 depicts flow a diagram that illustrates a method of calibration of a force-sensing catheter in accordance with an embodiment of the present invention. The process of calibration and compensation for component drift begins at step 100. At step 110 the probe is positioned (or repositioned) in a body cavity of the patient, more particularly, in the preferred embodiment, a catheter is manipulated so that the distal end is in the body cavity of the patient. As discussed above, the catheter preferably includes a force sensor 64 and a location sensor 62. A signal from the force sensor 64 is received by processor 40 at step 120. This signal will vary over time as the force sensed at the distal tip 34 of probe 32 varies over time as the tip comes in and out of contact with tissue in the body cavity. At step 130, data or images from one or more sources is input to verify contact of the tip of the catheter with the tissue of the patient. As discussed previously, this input can be electrocardiogram (ECG) data or impedance taken as an electrical signal form an electrode on probe 32 such as tip electrode 60 or can be image data such as fluoroscopic images, real-time CT-images, real-time magnetic resonance (MRI) images or images or data from an electro-anatomic mapping system. The processor 40 may be programmed to automatically recognize tissue contact based on electrical ECG or impedance signals or the processor may request user input based on the visual image data to determine tissue contact. The processor 40 may also be programmed to determine tissue contact based on the distance the probe 32 is from reconstructed tissue maps from an electro-anatomic mapping system such as the Carto® system. If the distance (d) is greater than a pre-determined threshold the processor 40 can be programmed to assume that the probe 32 is not in contact with the tissue of the patient. Using either type of decision process, at step 140 it is determined whether the probe 32 has contact with the tissue of the patient. If there is no contact the process branches to step 150 where the force signal taken at step 120 is set as the baseline or "zero" point for future readings, i.e., future force readings use this reading as the offset to determine the number of grams of force based on subsequent force sensor input. Alternatively, the system may ask for user input to confirm that the user would like to "re-zero" the readings from the force sensor rather than having this done automatically. At step 160, location data is input from the location sensor 62 on probe 32 providing at least three-dimensional spatial coordinates and preferably three degrees of orientation of the distal tip 34 of probe 32. This location information is then stored at step 170 in a look-up table of auto zero zones for later use.

At step 180, the probe may be repositioned as the probes in cardiac and other medical procedures are routinely repositioned during the procedure. In an alternative embodiment of the present method set forth at step 190, the location of the probe is continuously monitored and compared to the list of stored zeroing zone locations in the table created at step 170. If the processor 40 determines at step 190 that the probe 32 is in a location equivalent to one in the zeroing zone table then the force signal at that location will again be used as the baseline reading, i.e., the force reading reported to the user will be zero for the force signal input from force sensor 64 in probe 32. In this manner, the force sensing probe will be automatically recalibrated each time the location of the probe enters one of the stored zeroing zone locations.

If at step 190, it is determined that the probe is not in a location in the zeroing zone table then the signal from the force sensor will be input along with the verification data and/or images at step 130 and the tissue contact verification query will be reiterated at step 140. Once tissue contact is determined at step 140, the input from the force sensor 64 will be used to determine a force reading usually displayed on display 44 to the operator 28. The force reading is usually displayed in grams but may be displayed in other units of measurement.

The corresponding structures, materials, acts and equivalents of all means or steps plus function elements in the claims below are intended to include any structure, materials or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those skilled in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It will be appreciated that the embodiments described above are cited by way of example and that the present invention is not limited to what has been particularly shown and described hereinabove. Rather, the scope of the present invention includes both combinations and sub-combinations of the various features described hereinabove, as well as variations and modifications that would occur to persons skilled in the art upon reading the foregoing description and which are not disclosed in the prior art.

What is claimed is:

1. A method for calibrating a probe having a distal tip and force sensor near the distal end of the probe comprising the steps of:
   inserting the probe into a body cavity of a patient;
   receiving location information at a signal processor indicative of the location of the distal tip of the probe in a three-dimensional space;
   creating an anatomic image of a body cavity and storing image data representative of the location of the body cavity in the three-dimensional space in the signal processor;
   receiving at the signal processor a first signal from the force sensor indicative of the force being applied to the distal end of the probe;
   automatically verifying that the distal tip of the probe is not in contact with tissue of the patient independent of the first signal by using the signal processor to compare the location information indicative of the location of the distal tip of the probe to the anatomic image of the body cavity in the three-dimensional space;
   after the automatic verification step automatically calibrating the processor to set the first signal from the force sensor to a force reading of zero in response to verification that the force sensor is not in contact with tissue.

2. The method of claim 1 further comprising the step of:
   storing the location of the distal tip of the probe as a location of an auto zero zone.

3. The method of claim 2 further comprising the steps of:
   manipulating the probe to a stored auto zero zone location;
   receiving at the signal processor a second signal from the force sensor indicative of the force being applied to the distal end of the probe;
   recalibrating the processor to set the second signal from the force sensor to a force reading of zero.

4. The method of claim 2 further comprising the steps of:
   continuously monitoring the location of the distal tip of the probe in three-dimensional space;
   receiving at the signal processor a second signal from the force sensor indicative of the force being applied to the distal end of the probe;
   recalibrating the processor to set the second signal from the force sensor to a force reading of zero when the location of the distal tip of the probe is equivalent to an auto zero zone location.

5. The method of claim 2 wherein the step of receiving location information regarding the distal tip of the catheter comprises receiving the spatial coordinates and pitch, roll and yaw of the location sensor.

6. The method of claim 2 wherein the auto zero zone is expanded from a single point using reconstructed tissue geometry from an electro-anatomic mapping system to determine a three-dimensional auto zero zone around the single auto zero zone location that has been verified and located.

7. The method of claim 2 wherein the auto zero zone is expanded from a single point using reconstructed tissue geometry from an electro-anatomic mapping system to determine a three-dimensional auto zero zone around the single auto zero zone location that has been verified and located.

8. The method of claim 1 wherein the step of verifying comprises using a least one of electrocardiogram data, electrode impedance data, fluoroscopic imaging, real-time MM, real-time CT or electro-anatomic mapping system images or data to determine whether the distal tip of the probe is in contact with tissue of the patient.

9. The method of claim 1 wherein the probe comprises a cardiac catheter.

10. The method of claim 9 wherein the cardiac catheter is an ablation catheter having an electrode at the tip and wherein the tip electrode can also be used to record ECG data and/or impedance data.

11. The method of claim 1 wherein the body cavity comprises a chamber of a heart.

12. A system for re-calibrating force sensing probes comprising:
    a probe having a distal end and capable of being inserted into a body cavity of a patient and comprising a force sensor that provides a plurality of signals over time indicative of the force applied to the probe as the force varies over time;
    a location sensor operatively connected to the distal end of the probe and being configured to output a plurality of electrical signals indicative of the location of the probe within a three-dimensional space;
    an imaging system configured to create anatomic image data of the body cavity within the three-dimensional space; and
    a processor configured to compare the plurality of electrical signals indicative of the location of the probe within the three-dimensional space to the anatomic image data of the body cavity within the three-dimensional space and automatically determine if the probe is in contact with tissue in the body cavity of the patient independent of the force sensor signal;
    the processor further configured to receive the plurality of signals indicative of the force and generating a force reading indicative of the force on the probe wherein the processor sets the force reading to zero when the processor automatically determines that there is no contact between the probe and the body cavity of the patient.

13. The system of claim 12 wherein the location of the probe is stored in memory as an auto zero zone when there is no contact between the probe and the body cavity of the patient at the given location.

14. The system of claim 13 wherein the processor monitors the location of the probe and resets the force reading to zero when the probe is at a location stored in memory as an auto zero zone.

15. The system of claim 14 wherein the auto zero zone locations are stored with information regarding the point in the cardiac cycle at which the location information was taken.

16. The system of claim 14 wherein the auto zero zone locations are stored with information regarding the point in respiratory cycle at which the location information was taken.

17. The system of claim 12 wherein the probe is an electrophysiology catheter.

18. The system of claim 17 wherein the electrophysiology catheter has at least one electrode mounted on the distal end of the catheter.

19. The system of claim 18 wherein the plurality of electrical signals is based on electrocardiogram and/or impedance signals from at least one of the electrodes.

20. The system of claim 12 wherein the image data of the body cavity within the three-dimensional space is a fluoroscopic image.

21. The system of claim 12 wherein the image data of the body cavity within the three-dimensional space is a real-time CT image.

22. The system of claim 12 wherein the image data of the body cavity within the three-dimensional space is a real-time magnetic resonance image (MM).

23. The system of claim 12 wherein the image data of the body cavity within the three-dimensional space is data and/or images from an electroanatomic mapping system.

24. The system of claim 23 where the distance between the probe and the tissue of the patient based on data from the electro-anatomic mapping system is used to determine if there is tissue contact.

25. The system of claim 24 wherein the system automatically assumes there is no tissue contact if the distance between the probe and the tissue of the patient exceeds a pre-determined threshold.

26. The system of claim 12 wherein the location sensor is a magnetic location sensor capable of providing the processor with three-dimensional location coordinates and three degrees of orientation of the probe.

* * * * *